United States Patent [19]

Szur

[11] 4,093,775

[45] June 6, 1978

[54] TREATING A POLYMERIC SHAPE WITH NONIONIC FLUOROCHEMICAL SURFACTANTS AND PRODUCT THEREFROM

[75] Inventor: Alex J. Szur, North Plainfield, N.J.

[73] Assignee: Diamond Shamrock Corporation, Cleveland, Ohio

[21] Appl. No.: 680,787

[22] Filed: Apr. 27, 1976

Related U.S. Application Data

[62] Division of Ser. No. 560,698, March 21, 1975, Pat. No. 3,980,715.

[51] Int. Cl.$^2$ ................ B32B 27/00; D02G 3/00
[52] U.S. Cl. .................................. 428/394; 428/395; 428/421; 428/474; 428/543; 428/96; 260/615 F; 260/615 BF; 427/323; 427/324; 427/389; 427/390 B
[58] Field of Search ............... 428/543, 394, 395, 421, 428/474; 260/615 F, 615 BF

[56] References Cited

U.S. PATENT DOCUMENTS

| | | | |
|---|---|---|---|
| 2,723,999 | 11/1955 | Cowen et al. | 260/615 BF |
| 3,459,722 | 8/1969 | Zanger | 428/395 X |
| 3,916,053 | 10/1975 | Sherman et al. | 428/395 X |
| 3,952,075 | 4/1976 | Nakamura et al. | 260/615 F X |

*Primary Examiner*—P. C. Ives
*Attorney, Agent, or Firm*—Neal T. Levin; Leslie G. Nunn

[57] ABSTRACT

6-Hydroxyhexyl perfluoroisopropyl ether is prepared by reaction of hexafluoroacetone and potassium fluoride to obtain an alcoholate which is then reacted with 1-chloro-6-hexanol. One mole of the ether may be reacted with about 1 mole to about 20 moles of ethylene oxide. One mole of 2,2,3,4,4,4-hexafluorobutanol may also be reacted with about 1 mole to about 6 moles of propylene oxide and then about 1 mole to about 20 moles of ethylene oxide. Both ethoxylates are nonionic surfactants which are useful as antistatic agents and lubricants for polymeric shapes such as nylon films and filaments.

30 Claims, No Drawings

TREATING A POLYMERIC SHAPE WITH NONIONIC FLUOROCHEMICAL SURFACTANTS AND PRODUCT THEREFROM

This is a divisional of application Ser. No. 560,698, filed Mar. 21, 1975, now U.S. Pat. No. 3,980,715, patented Sept. 14, 1976.

BACKGROUND OF THE INVENTION

1. Field of the Invention

This invention relates to nonionic fluorochemical surfactants useful as antistatic agents and lubricants for polymeric shapes.

2. Description of the Prior Art

U.S. Pat. 3,702,870 — Pittman et al, issued Nov. 14, 1972, and U.S. Pat. 3,758,538 — Litt et al, issued Sept. 11, 1973, describe preparation of fluorinated alcoholates by reaction of a fluoroketone with an alkali metal fluoride. In Pittman et al, the alcoholates are then reacted with acyl halides to obtain esters useful in improving water-repellency and oil-repellency of textiles. In Litt et al, the alcoholates are then reacted with olefins to obtain fluorine containing ethers useful as surfactants.

U.S. Pat. No. 2,723,999 — Cowen et al. issued Nov. 15, 1955, describes preparation of nonionic surfactants by reaction of fluorinated alcohol with ethylene oxide.

Although these patents teach preparation of fluorinated surfactants, there is a definite need for improved fluorinated surfactants having useful properties as antistatic agents and lubricants for polymeric shapes.

STATEMENT OF THE INVENTION

Fluorochemical nonionic surfactants are prepared:

(A) by reaction of hexafluoroacetone and potassium fluoride to obtain an alcoholate which is then reacted with 1-chloro-6-hexanol to obtain 6-hydroxyhexyl perfluoroisopropyl ether which is then reacted with ethylene oxide, and (B) by reaction of 2,2,3,4,4,4-hexafluorobutanol with propylene oxide and then with ethylene oxide to obtain useful nonionic fluorochemical surfactants. These surfactants include the reaction product of 6-hydroxyhexyl perfluoroisopropyl ether with from about 1 to about 20 moles of ethylene oxide and the reaction product of hexafluorobutanol with from about 1 to about 6 moles of propylene oxide and with from about 1 to about 20 moles of ethylene oxide. These nonionic surfactants are useful as antistatic agents, lubricants and antisoiling agents for polymeric shapes such as nylon films and filaments.

DESCRIPTION OF THE PREFERRED EMBODIMENTS

The fluorochemical surfactants of the present invention are nonionic surfactants derived from low priced commercial fluorochemicals. These surfactants may be prepared from hexafluoroacetone and 2,2,3,4,4,4-hexafluorobutanol.

Several synthetic routes are available to extend the hydrophobic chain of these starting materials and to introduce the desired hydrophilic functionality required in surfactants. For example, the acetone may be reacted with potassium fluoride in diglyme to obtain the alcoholate, potassium heptafluoroisopropoxide shown in Reaction (I).

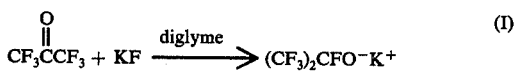

Other alkali metal alcoholates such as sodium heptafluoroisopropoxide, lithium heptafluoroisopropoxide and the like may be used. The potassium heptafluoroisopropoxide may then be reacted with 1-chloro-6-hexanol to obtain the ether-alcohol shown in Equation (II).

Likewise, 2,2,3,4,4,4 hexafluorobutanol may be reacted with propylene oxide (PO) to obtain the polyethers shown in Equation (III).

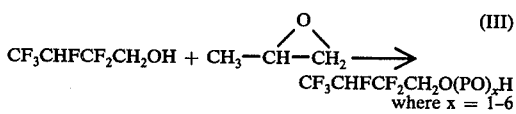

Hydrophilic functionality may then be introduced into reaction products of Equations II and III. For example, the ether-alcohol reaction product of Equation II may be ethoxylated with ethylene oxide (EO) to obtain the ethoxylates shown in Equation (IV).

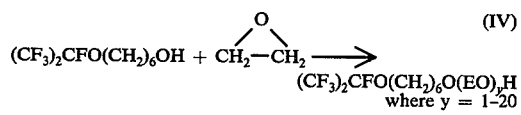

and similarly, the propoxylated intermediate of Equation III may be reacted with ethylene oxide to obtain ethoxylates shown in Equation (V).

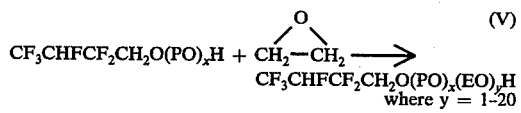

Antistatic properties of treated polymeric shapes such as filaments or films containing from about 0.1 to about 5% by weight of one of the above surfactants based on the weight of the shape may be determined using the procedure described by M. J. Schick in Friction and Lubrication of Synthetic Fibers, Part I, Textile Research Journal, Vol. 43, No. 2, pp. 103-109 (February 1973). In this procedure, a given charge is placed on a polymeric shape such as a yarn specimen and the time required for one-half of the charge of the shape to dissipate from the shape is measured and recorded as the antistatic half-life.

Lubricity properties of shapes treated with one of the above surfactants may be determined by the procedure given in the above mentioned publication or by the procedure using the tripod sled apparatus as described by M. J. Schick, T. F. MacDonnell and J. H. Nash in Wear 25, (1973) pp 385-392. Both procedures are described in greater detail in the examples below.

Further, tendency of these surfactants to improve antisoiling properties of shapes such as carpeting may be evaluated by the procedure described in the examples.

The surfactant may be applied directly to the polymeric shape by any known method such as by means of a spray, by means of a bath, by means of an aqueous solution or dispersion or by means of a solvent such as a solution of the surfactant in a solvent such as chlorinated hydrocarbon, water or the like. If desired, the surfactant may be applied in solvent free form. Likewise, the surfactant may be compounded with the polymeric material prior to shaping in the form of a filament, film, foil or the like. These application methods are well known in the art.

The surfactants of this invention may be used to treat various textile fibers. These fibers include natural, man-made and synthetic fibers such as cotton, wool, silk, jute, sisal, hemp, fur, flax, kapok, rayon, cellulose acetate, cellulose triacetate, polyamides such as nylon, polyesters such as polyethylene terephthalate (Dacron), acrylics such as polyacrylonitrile, vinyl resins such as copolymers of polyvinyl chloride and polyvinyl acetate, copolymers of vinylidene chloride and vinyl chloride, copolymers of acrylonitrile and vinyl chloride, or the like, polystyrene, polyethylene, polypropylene, polyurethane, glass, ceramic, asbestos, protein fibers such as vicara and penaut protein, blends of these and the like. Blends of several fibers may be used. The term fiber includes textile materials in the form of fibers, continuous or spun yarns, filaments, rovings, slivers, tops and the like.

For a fuller understanding of the nature and objects of this invention, reference may be made to the following examples which are given merely to illustrate the invention and are not to be construed in a limiting sense. All weights, proportions and percentages are on a weight basis unless otherwise indicated. Likewise, all temperatures are °C. unless otherwise indicated.

EXAMPLE I

This example describes the preparation of an ethoxylate of 6-hydroxyhexyl perfluorisopropyl ether.

6-Hydroxyhexyl perfluoroisopropyl ether

A 1 l., four-necked flask, fitted with a stirrer, thermometer, gas inlet tube, addition funnel and dry ice condenser, was purged with nitrogen and charged with 200 ml of diglyme and 21.3 g (0.37 m) of potassium fluoride. The slurry was cooled to −40° C in an isopropanol-dry ice bath and 66 g (0.4 m) of hexafluoroacetone added over a period of 45 minutes. After the addition was completed, the reaction mixture was allowed to warm to room temperature and become a clear solution of potassium heptafluoroisopropoxide.

1-Chloro-6-hexanol (50 g, 0.37 m) was added allowing the exotherm to raise the temperature to 36° C. After the addition was completed, the reaction mixture was heated at 40° C for 2 hours. The reaction mixture washed with a sodium chloride solution and vacuum distilled to yield 28 g of clear, colorless liquid 6-hydroxyhexyl perfluoroisopropyl ether b.p. 119°–122° C/18 mm, $n_d^{21.5}$ 1.4278. IR analysis showed the following major absorption bands: 3400, 2940, 2862, 1220, 1090 cm$^{-1}$.

Ethoxylation of 6-hydroxyhexyl perfluoroisopropyl ether

A 250 ml four-necked flask fitted with stirrer, thermometer, gas inlet and outlet was charged with 42 g (0.15 m) 6-hydroxyhexyl perfluoroisopropyl ether and 0.1 g of boron trifluoride etherate and purged with nitrogen at room temperature. The mixture was heated to 40° C and ethylene oxide (total 76.9 g, 1.75 m) was added with stirring maintaining the temperature at approximately 40° C with a cooling bath. Samples were removed at 49.6 wt % (6.4 m) designated as Product I (A), 57.5 wt. % (8.8 m) designated as Product I (B) and 67.2 wt % (13.4 m) designated as Product I (C) ethylene oxide. The reaction was terminated at 67.2 wt % (13.4 m) ethylene oxide. The three products were all clear, colorless liquids with $n_d^{23}$ (respectively): 1.4449, 1.4485, 1.4508. IR analysis of the three samples showed the following major absorption bands: 3460, 2940, 2860, 1240, 1110 cm$^{-1}$.

EXAMPLE II

This example describes the propoxylation and ethoxylation of 2,2,3,4,4,4-hexafluorobutanol.

2,2,3,4,4,4-Hexafluorobutanol plus 2 moles of propylene oxide

To a 500 ml four-necked flask fitted with a stirrer, thermometer, addition funnel and dry ice condenser was charged 91 g (0.5 m) of 2,2,3,4,4,4-hexafluorobutanol and 0.3 g of boron trifluoride etherate solution. The reaction flask contents were purged with nitrogen at room temperature and then heated to 40° C. Propylene oxide (93 g, 1.6 m) was added slowly from the addition funnel while maintaining the temperature at 40° C. Stirring was continued after the addition was completed until the exotherm subsided. The reaction mixture was stripped under vacuum 40° C/7mm yielding the 2 mole propoxylate of 2,2,3,4,4,4-hexafluorobutanol with a hydroxyl number of 189, calc 188 for 2 mole propoxylate. IR analysis showed the following major absorption bands: 3390, 2985, 2935, 2890, 1190, 1100 cm$^{-1}$.

2,2,3,4,4,4-Hexafluorobutanol plus 4 moles of propylene oxide

To a 250 ml four-necked flask fitted with a stirrer, thermometer, addition funnel and dry ice condenser was charged 50 g (0.27 m) of 2,2,3,4,4,4-hexafluorobutanol and 0.2 g. of boron trifluoride etherate solution. The reaction flask contents were purged with nitrogen at room temperature and then heated to 40° C. Propylene oxide 51 g (0.88 m) was added slowly from the addition funnel while maintaining the temperature at 40° C. Stirring was continued after the addition was completed until the exotherm subsided. The reaction mixture was stripped under vacuum 50° C/10mm yielding the 4 mole propylate of 2,2,3,4,4,4-hexafluorobutanol with a hydroxyl number of 135.9, calc 135.5 for 4 mole propoxylate.

Ethoxylation of the 2 mole propoxylate of 2,2,3,4,4,4-hexafluorobutanol

To a 250 ml four-necked flask fitted with a stirrer, thermometer and gas inlet and outlet was charged 44 g (0.15 m) of the 2 mole propoxylate of 2,2,3,4,4,4-hexafluorobutanol and 0.3 g of boron trifluoride etherate solution. The reaction flask contents were purged with nitrogen at room temperature and then heated to 40° C. Ethylene oxide (98.2 g, 2.23 m total) was added maintaining the temperature at approximately 40° C with cooling. Samples were removed at 50 wt % (6.8 m) ethylene oxide designated as Product II (A), at 62 wt % (11.1 m) ethylene oxide designated as Product II (B) and at 71.6 wt % (17.1 m) ethylene oxide designated as Product II (C). The reaction was terminated at 71.6 wt % (17.1 m) ethylene oxide. The three products were clear, colorless to light yellow liquids with $n_d^{23.5}$ (respectively): 1.4265, 1.4309 and 1.4365. IR analysis showed the three products to have major absorption bands at 3460, 2970, 2870, 1190, 1100 cm$^{-1}$.

EXAMPLE III

Lubricating properties of the above fluorochemical surfactants, Products of Example I (A), I (B), I (C), II (A), II (B) and II (C), were determined using the following procedure. Coefficient of friction of each surfactant was measured using a Rothschild F-Meter 1081 for Measuring Coefficients of Friction (formerly Haberline, Inc., Raleigh, N. C., now Lawson-Hemphill Sales, Inc., Spartanburg, S. C.) with two Rothschild Electronic Tensiometers (formerly Haberline, Inc., Raleigh, N. C., now Lawson-Hemphill Sales, Inc., Spartanburg, S. C.), as described by M. J. Schick in Friction and Lubrication of Synthetic Fibers, Part I, Textile Research Journal, Vol. 43, No. 2, pp. 103–109 (February 1973). The surfactant was applied at 1% by weight based on the weight of fiber to the fiber and the treated fiber conditioned for 24 hours at 50% relative humidity and 72° F. The coefficient of friction of the conditioned fiber was then measured using the apparatus described above in the following procedure.

An aqueous or isopropanol solution or dispersion of each surfactant was applied to a sample of 200/34 nylon filament yarn. Each yarn sample was then dried to remove water or alcohol and conditioned for 24 hours at 50% relative humidity and 72° F. The conditioned, treated yarn sample, which contained 1% by weight of the surfactant based on the weight of the fiber, was then evaluated to determine the fiber to metal coefficient of friction at 50% relative humidity and 72° F. Coefficients of fiber to metal friction were measured using the Rothschild F-Meter 1081 with two Rothschild Electronic Tensiometers. Incoming tension on the yarn was 0.5 g per denier and the friction surface was a 0.5 inch diameter chrome pin having a roughness value of 52 RMS. Yarn was wrapped around the pin circumference once. Yarn speeds were: 5.5, 55, 100 and 300 yards per min. Results of these friction tests are shown in Table I below.

Antistatic properties of the conditioned, treated yarn samples were also determined. The antistatic half-life test used in these measurements is the test described in the above publication. In this test, a given charge is placed on a yarn specimen and the time required for one half of the charge on the specimen to dissipate from the test specimen is measured and recorded as the antistatic half-life of the treated fiber. Results of these tests are shown as the Antistatic Half-Life Seconds in Table I below.

TABLE I

COEFFICIENTS OF FRICTIONS AND ANTI-STATIC PROPERTIES (1)

| Product of Example | Speed (Yds/Min) | Coefficient of fiber to metal friction | Anti-Static Half-Life Seconds |
|---|---|---|---|
| Butyl Stearate | 5.5 | 0.160 | 36,000 |
| | 55 | 0.160 | |
| | 100 | 0.173 | |
| | 300 | 0.186 | |
| T (A) | 5.5 | 0.198 | 1,050 |
| | 55 | 0.238 | |
| | 100 | 0.270 | |
| | 300 | 0.296 | |
| I (B) | 5.5 | 0.160 | 1,600 |
| | 55 | 0.198 | |
| | 100 | 0.220 | |

TABLE I-continued

COEFFICIENTS OF FRICTIONS AND ANTI-STATIC PROPERTIES (1)

| Product of Example | Speed (Yds/Min) | Coefficient of fiber to metal friction | Anti-Static Half-Life Seconds |
|---|---|---|---|
| | 300 | 0.238 | |
| I (C) | 5.5 | 0.160 | 2,050 |
| | 55 | 0.186 | |
| | 100 | 0.210 | |
| | 300 | 0.230 | |
| II (A) | 5.5 | 0.186 | 577.5 |
| | 55 | 0.238 | |
| | 100 | 0.263 | |
| | 300 | 0.278 | |
| II (B) | 5.5 | 0.144 | 489.5 |
| | 55 | 0.220 | |
| | 100 | 0.238 | |
| | 300 | 0.263 | |
| II (C) | 5.5 | 0.144 | 236.5 |
| | 55 | 0.220 | |
| | 100 | 0.238 | |
| | 300 | 0.263 | |

(1) 1% by weight on nylon 200 DuPont at 72° F, 50% humidity, 1 loop on chrome pin.

EXAMPLE IV

Each of the above fluorochemical surfactants (Products of Example I (A), I (B), I (C), II (A), II (B) and II (C)) was applied to the surface of nylon 66 film at a concentration of about 1% by weight of surfactant based on weight of the film. Each sample conditioned for one week at 50% relative humidity and 72° F prior to testing and then tested under these conditions. Frictional properties were determined by the procedure using the tripod sled apparatus described by M. J. Schick, T. F. MacDonnell and J. H. Nash in *Wear* 25, (1973) pp 385–392 to determine the coefficient of friction for film to metal boundary lubrication at a relative surface speed of 3 inches per minute and at three loads: 300 g, 600 g and 900 g. Frictional force was measured using a Statham Transducer (Statham Medical Instrument, Inc., Hato Rey, Puerto Rico) and recorded on a Sanborn Recorder 150 equipped with a carrier preamplifier (Hewlett Packard Co., Palo Alto, California). The coefficient of friction, $f = F/W$ where $f$ signifies the frictional coefficient, $F$ the frictional force and $W$ the normal load, was then calculated from the average measured force divided by the load. A blank sample was also tested by the same procedure. Results of these tests are shown in Table II. These results show that the friction of the treated samples is lower than the blank sample.

TABLE II

COEFFICIENTS OF FRICTION (METAL-NYLON), TRIPOD SLED

| Product of Example | Coefficient of Friction | | |
|---|---|---|---|
| | 300 gms. | 600 gms. | 900 gms. |
| Blank | 0.16 | 0.16 | 0.13 |
| I (A) | 0.09 | 0.09 | 0.09 |
| I (B) | 0.08 | 0.08 | 0.08 |
| I (C) | 0.06 | 0.07 | 0.08 |
| II (A) | 0.06 | 0.07 | 0.08 |
| II (B) | 0.05 | 0.07 | 0.06–0.10 |
| II (C) | 0.05 | 0.07 | 0.05–0.09 |

EXAMPLE V

In the carpet soiling test, the relative tendency of carpet samples to retain soil was measured by application of about 2 g of a synthetic soil containing

| Ingredient | % By Weight |
| --- | --- |
| Michigan peat | 42.75 |
| Cement | 17.00 |
| Silica | 17.00 |
| Koalin | 17.00 |
| Mineral Oil | 4.00 |
| Carbon Black | 1.75 |
| Red Iron Oxide | 0.50 |

The soil was prepared by pebble milling the above ingredients for 35 hours and then drying the mixture at 100° C for 5 hours. To avoid variations, sufficient soil was prepared to complete a series of soiling tests.

The soil was applied to the carpet samples using a can having both ends removed, measuring 5 inches length × 3 inches diameter and having two 2 × 1½ inches windows on the circumference. The can was mounted on 5 inches diameter discs at both ends. One of the discs also served as the lid for the can. Mounted in the center of the inside of the lid was a fine mesh wire basket, (3 × ¾ inches diameter) to hold and distribute 2 g of synthetic soil. A hose clamp, 3½ × 4 inches diameter, was used to secure the carpet samples firmly against the windows. Auxiliary equipment included six ½ inches diameter steel balls and a vacuum cleaner.

The soil was applied using the following procedure. Carpet samples (3 × 3½ inches) with finish removed by scour or extraction were padded with 1% by weight solutions of each test fluorochemical to obtain a 100% weight pickup. The padded carpet samples were dried in an oven at 100° C. Approximately 2 g of synthetic soil (dried at 100° C for 2 hours before use) was placed in the wire basket and the six steel balls were placed in the can. Then the apparatus was assembled and rotated on a ball mill for 5 minutes in each direction. The ball mill was stopped and the carpet samples were removed. Loose soil was vacuumed off of the surface of the samples using ten strokes in each direction. Soiling was evaluated visually comparing samples with an untreated sample of carpet as a blank. Results of these tests are as follows:

| Products of Example | Appearance of Carpet Compared to Untreated Sample |
| --- | --- |
| I (C) | equivalent to untreated sample with litter or no soil |
| II (A) | slightly smeared |
| I (A) | smeared |
| I (B) | smeared |
| II (C) | smeared |
| II (B) | smeared |

While the invention has been described with reference to certain specific embodiments thereof, it is understood that it is not to be so limited since alterations and changes may be made therein which are within the full intended scope of the appended claims.

What is claimed is:

1. A process of treating a polymeric shape with an effective amount of a nonionic fluorochemical surfactant selected from the group consisting of:
   (a) condensation product of one mole of 6-hydroxyhexyl perfluoroisopropyl ether with from about 1 to about 20 moles of ethylene oxide, and
   (b) condensation product of one mole of 2,2,3,4,4,4-hexafluorobutanol with from about 1 to about 6 moles of propylene oxide and with from about 0 to about 20 moles of ethylene oxide to improve lubricity properties, antistatic properties and antisoiling properties of the shape.

2. The process of claim 1 wherein from about 0.1 to about 5% of the surfactant based on the weight of the polymeric shape is applied to the shape.

3. The process of claim 1 wherein the shape is treated to improve lubricity properties.

4. The process of claim 1 wherein the shape is treated to improve antistatic properties.

5. The process of claim 1 wherein the shape is treated to improve antisoiling properties.

6. The process of claim 1 wherein the polymeric shape is nylon.

7. The process of claim 6 wherein the polymeric shape is nylon fiber.

8. The process of claim 1 wherein the surfactant is applied externally to the polymeric shape.

9. The process of claim 1 wherein the surfactant is incorporated internally in the polymeric shape.

10. A polymeric shape produced by the process of claim 1.

11. The process of claim 1 wherein the polymeric shape is treated with an effective amount of a condensation product of one mole of 6-hydroxyhexyl perfluoroisopropyl ether with from about 1 to about 20 moles of ethylene oxide to improve lubricity properties, antistatic properties and antisoiling properties of the shape.

12. The process of claim 11 wherein from about 0.1 to about 5% of the surfactant based on the weight of the polymeric shape is applied to the shape.

13. The process of claim 11 wherein the shape is treated to improve lubricity properties.

14. The process of claim 11 wherein the shape is treated to improve antistatic properties.

15. The process of claim 11 wherein the shape is treated to improve antisoiling properties.

16. The process of claim 1 wherein the polymeric shape is nylon.

17. The process of claim 11 wherein the polymeric shape is nylon fiber.

18. The process of claim 11 wherein the surfactant is applied externally to the polymeric shape.

19. The process of claim 11 wherein the surfactant is incorporated internally in the polymeric shape.

20. A polymeric shape produced by the process of claim 11.

21. The process of claim 1 wherein the polymeric shape is treated with an effective amount of a condensation product of one mole of 2,2,3,4,4,4-hexafluorobutanol with from about 1 to about 6 moles of propylene oxide and with from about 0 to about 20 moles of ethylene oxide to improve lubricity properties, antistatic properties and antisoiling properties of the shape.

22. The process of claim 21 wherein from about 0.1 to about 5% of the surfactant based on the weight of the polymeric shape is applied to the shape.

23. The process of claim 21 wherein the shape is treated to improve lubricity properties.

24. The process of claim 21 wherein the shape is treated to improve antistatic properties.

25. The process of claim 21 wherein the shape is treated to improve antisoiling properties.

26. The process of claim 21 wherein the polymeric shape is nylon.

27. The process of claim 21 wherein the polymeric shape is nylon fiber.

28. The process of claim 21 wherein the surfactant is applied externally to the polymeric shape.

29. The process of claim 21 wherein the surfactant is incorporated internally in the polymeric shape.

30. A polymeric shape produced by the process of claim 21.

* * * * *